(12) United States Patent
Lee

(10) Patent No.: US 9,402,602 B2
(45) Date of Patent: Aug. 2, 2016

(54) TISSUE SAMPLING APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 30 days.

(21) Appl. No.: 13/749,679

(22) Filed: Jan. 25, 2013

(65) Prior Publication Data

US 2014/0213931 A1   Jul. 31, 2014

(51) Int. Cl.
*A61B 10/02*  (2006.01)
*A61M 1/00*  (2006.01)

(52) U.S. Cl.
CPC ........... *A61B 10/0233* (2013.01); *A61B 10/025* (2013.01); *A61B 2010/0258* (2013.01); *A61M 1/008* (2013.01)

(58) Field of Classification Search
None
See application file for complete search history.

(56) References Cited

U.S. PATENT DOCUMENTS

| | | | |
|---|---|---|---|
| 4,543,966 A * | 10/1985 | Islam et al. | ............. 600/567 |
| 5,279,306 A | 1/1994 | Mehl | |
| 5,331,972 A | 7/1994 | Wadhwani | |
| 5,357,974 A | 10/1994 | Baldridge | |
| 5,456,267 A | 10/1995 | Stark | |
| 5,807,275 A | 9/1998 | Jamshidi | |
| 5,807,277 A | 9/1998 | Swaim | |
| 5,868,684 A | 2/1999 | Akerfeldt | |
| 5,885,226 A | 3/1999 | Rubinstein | |
| 5,910,121 A | 6/1999 | Paolo | |
| 6,015,391 A | 1/2000 | Rishton | |
| 6,019,776 A * | 2/2000 | Preissman et al. | ............. 606/185 |
| 6,022,324 A | 2/2000 | Skinner | |
| 6,033,369 A | 3/2000 | Goldenberg | |
| 6,063,037 A | 5/2000 | Mittermeier | |
| 6,080,115 A | 6/2000 | Rubinstein | |
| 6,110,128 A | 8/2000 | Andelin | |
| 6,179,853 B1 | 1/2001 | Sachse | |
| 6,221,029 B1 | 4/2001 | Mathis | |
| 6,264,618 B1 | 7/2001 | Landi | |
| 6,312,394 B1 | 11/2001 | Fleming | |
| 6,315,737 B1 | 11/2001 | Skinner | |
| 6,416,484 B1 | 7/2002 | Miller | |
| 6,443,910 B1 | 9/2002 | Krueger | |
| 6,478,751 B1 | 11/2002 | Krueger | |
| 6,554,778 B1 | 4/2003 | Fleming | |
| 6,730,043 B2 | 5/2004 | Krueger | |
| 6,755,793 B2 | 6/2004 | Lamoureux | |
| 6,849,051 B2 | 2/2005 | Sramek | |

(Continued)

FOREIGN PATENT DOCUMENTS

| CN | 201814597 U | 5/2011 |
|---|---|---|
| CN | 202027612 U | 11/2011 |

(Continued)

*Primary Examiner* — Devin Henson
*Assistant Examiner* — Matthew Kremer

(57) ABSTRACT

The current invention presents a tissue sampling apparatus and methods to reliably obtain solid and liquid bone marrow samples in sequence in a single insertion of the apparatus to a target area. The apparatus comprises a proximal handle assembly, a distal cutting assembly and a shaft assembly connecting both assemblies. The handle assembly comprises an upper handle connected to an inner cutting tube and a lower handle connected to an outer cannula. The lower handle transmits axial rotation of the upper handle to longitudinal movement of the inner cutting tube. Axial rotation of an engaged upper handle longitudinally pulls out from the outer cannula the inner cutting tube that spirally holds fast a solid marrow sample inside a distal end of said inner cutting tube. Following acquisition of the solid marrow sample, a liquid marrow sample is aspirated through the outer cannula.

7 Claims, 13 Drawing Sheets

(56) References Cited

U.S. PATENT DOCUMENTS

| | | |
|---|---|---|
| 6,875,183 B2 | 4/2005 | Cervi |
| 6,890,308 B2 | 5/2005 | Islam |
| 6,916,292 B2 | 7/2005 | Morawski |
| 6,942,669 B2 | 9/2005 | Kurc |
| 7,014,614 B2 | 3/2006 | Casula |
| 7,018,343 B2 | 3/2006 | Plishka |
| 7,081,123 B2 | 7/2006 | Merboth |
| 7,179,232 B2 | 2/2007 | Sutton |
| 7,201,722 B2 | 4/2007 | Krueger |
| 7,278,972 B2 | 10/2007 | Lamoureux |
| 7,331,930 B2 | 2/2008 | Faciszewski |
| 7,338,456 B2 | 3/2008 | Goldenberg |
| 7,384,400 B2 | 6/2008 | Goldenberg |
| 7,455,645 B2 | 11/2008 | Goldenberg |
| 7,608,049 B2 | 10/2009 | Goldenberg |
| 7,662,108 B2 | 2/2010 | Dunker |
| 7,731,667 B2 | 6/2010 | Goldenberg |
| 7,850,620 B2 | 12/2010 | Miller |
| 7,850,651 B2 | 12/2010 | Allee |
| 7,914,461 B2 | 3/2011 | Richard |
| 7,951,089 B2 | 5/2011 | Miller |
| 7,988,643 B2 | 8/2011 | Hoffmann |
| 8,070,689 B2 | 12/2011 | Masseglia |
| 8,070,690 B2 | 12/2011 | Ikehara |
| 8,096,957 B2 | 1/2012 | Conquergood |
| 8,167,899 B2 | 5/2012 | Justis |
| 2004/0127814 A1 | 7/2004 | Negroni |
| 2005/0267383 A1 | 12/2005 | Groenke |
| 2007/0010843 A1 | 1/2007 | Green |
| 2008/0119759 A1 | 5/2008 | McLain |
| 2008/0139961 A1 | 6/2008 | Slama |
| 2008/0262383 A1 | 10/2008 | Routhier |
| 2008/0281223 A1 | 11/2008 | Goldenberg |
| 2010/0069788 A1 | 3/2010 | Dell'Oca |
| 2010/0069790 A1 | 3/2010 | Green |
| 2010/0204611 A1 | 8/2010 | Zambelli |
| 2010/0234761 A1 | 9/2010 | Cortes Ramirez |
| 2011/0034884 A9 * | 2/2011 | Pellegrino et al. ............ 604/272 |
| 2011/0288438 A1 | 11/2011 | Lee |

FOREIGN PATENT DOCUMENTS

| | | |
|---|---|---|
| CN | 202069615 U | 12/2011 |
| GB | 2347862 A | 9/1999 |
| IT | WO 2004082484 A1 | 9/2004 |
| IT | WO 2005009246 A1 | 2/2005 |
| JP | EP 2022405 A1 | 7/2008 |
| WO | WO 9603081 A1 | 2/1996 |
| WO | WO 9627330 A1 | 9/1996 |
| WO | WO 03057045 A1 | 7/2003 |

* cited by examiner

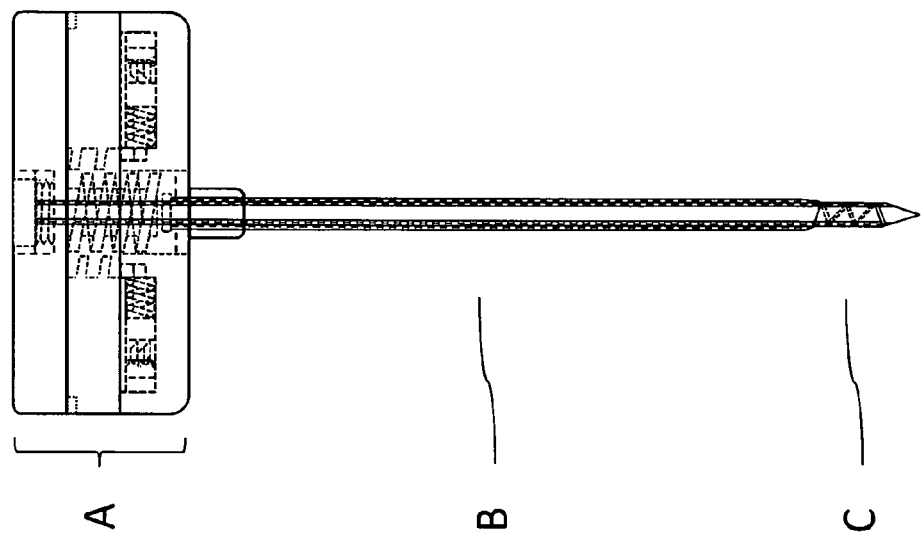

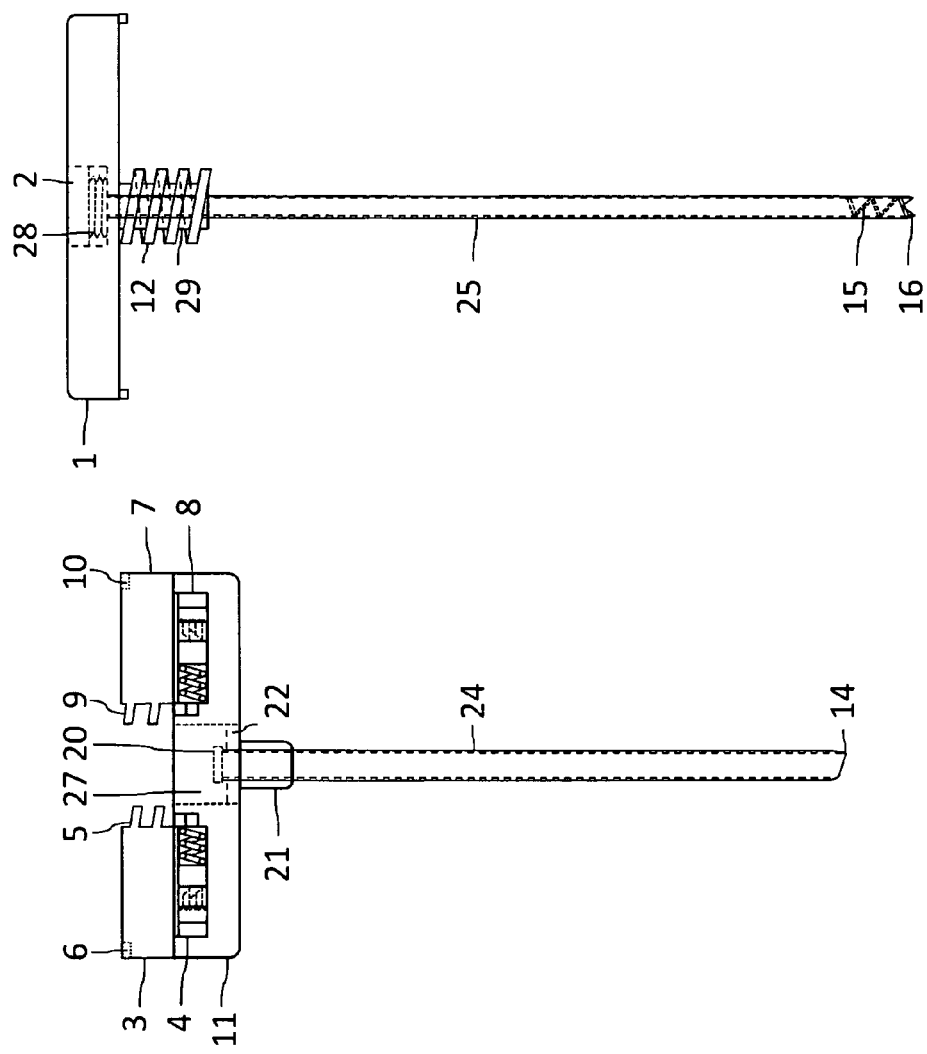

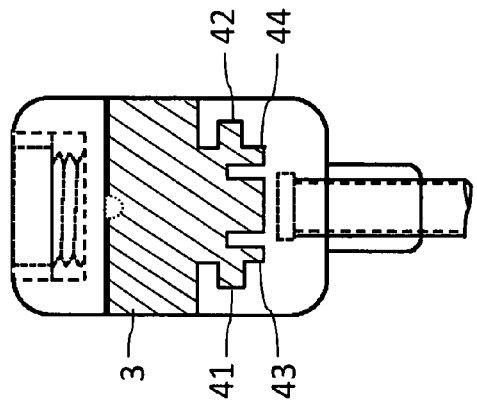
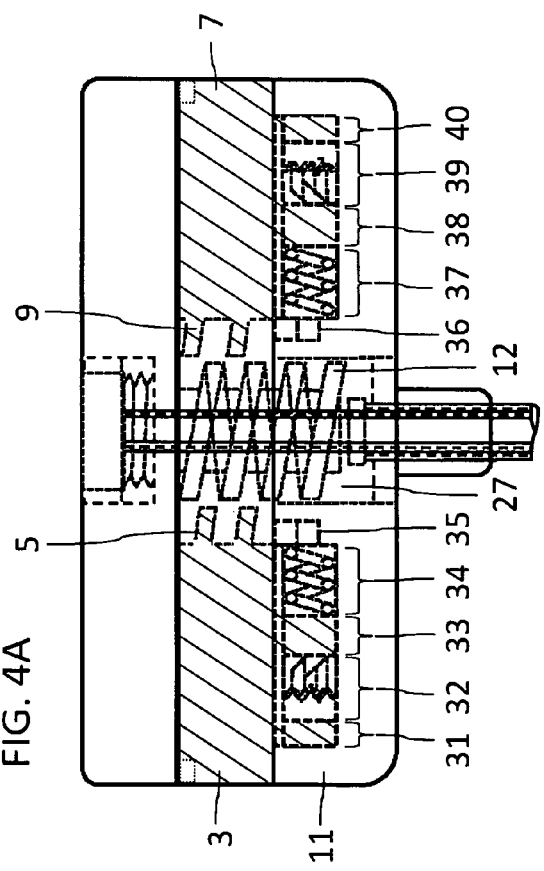
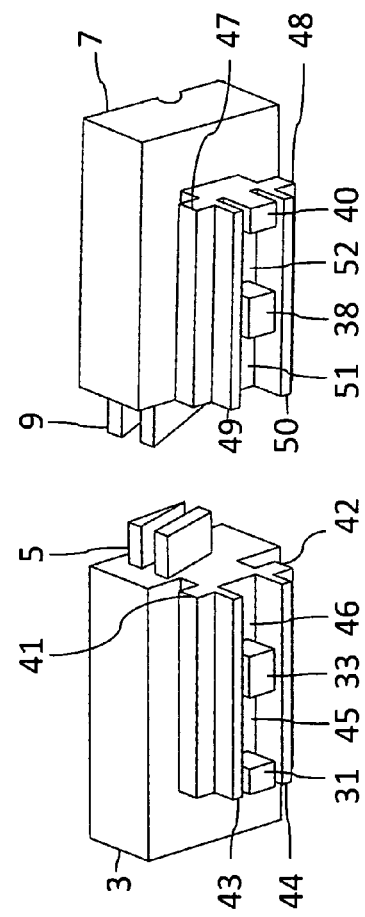

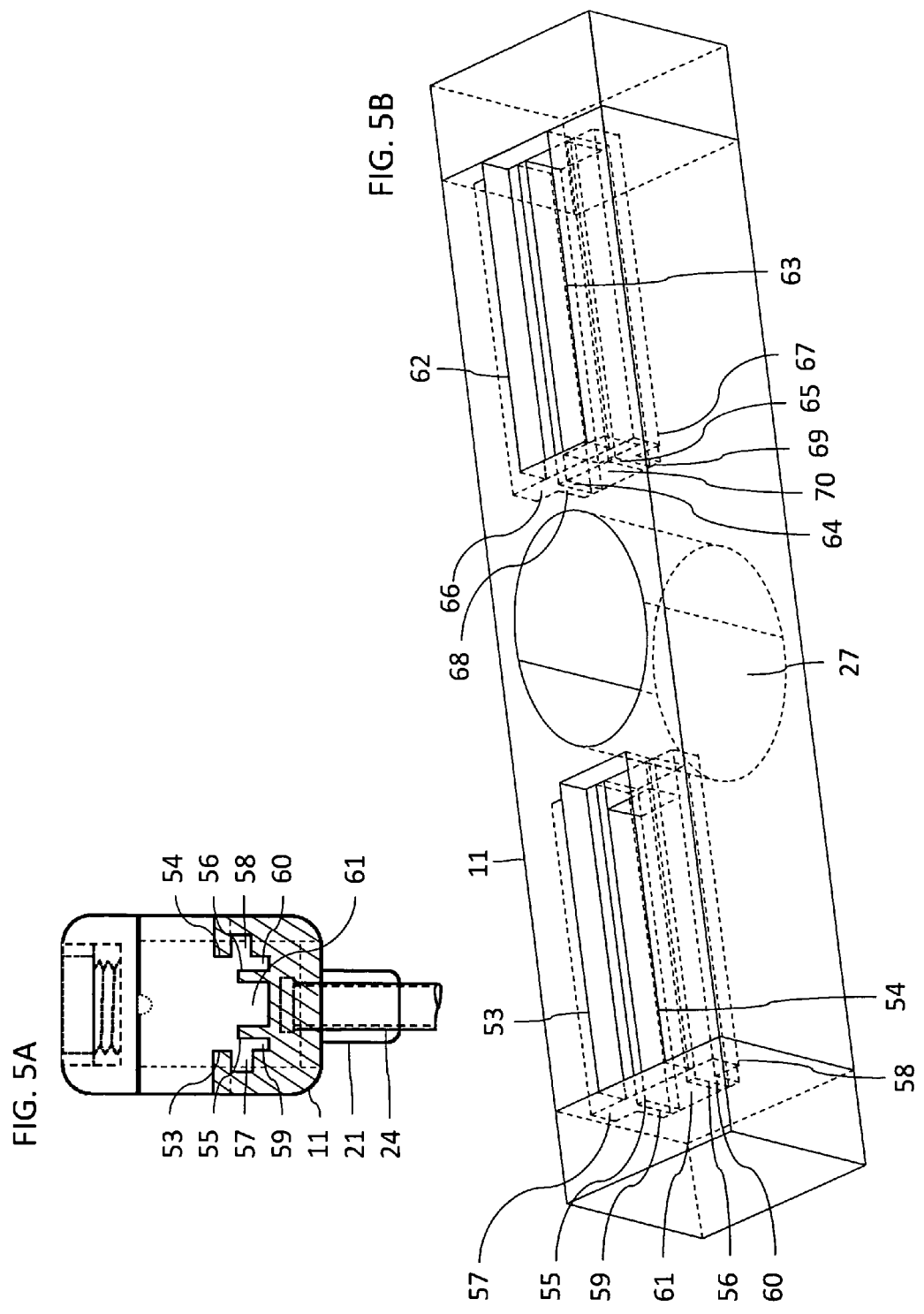

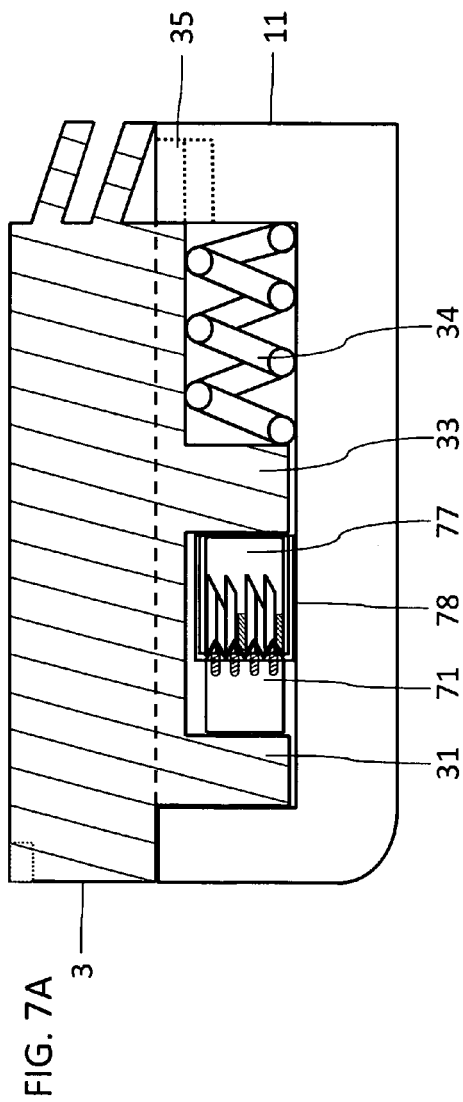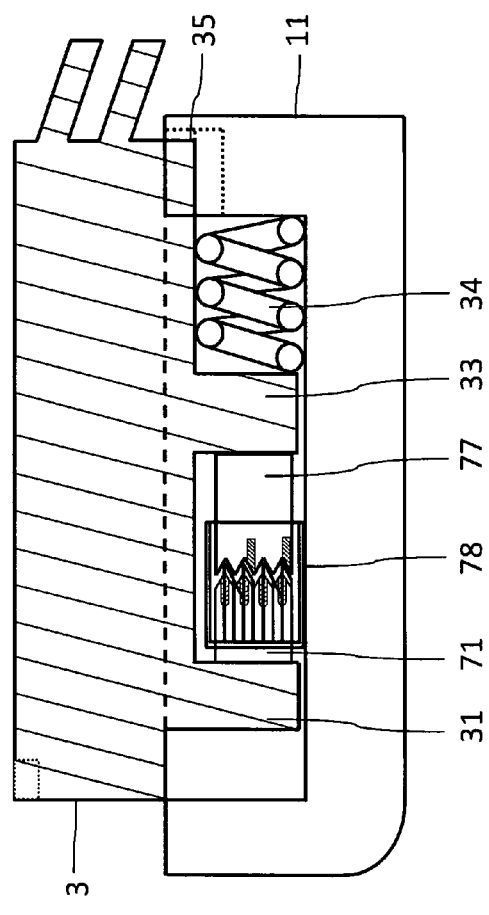

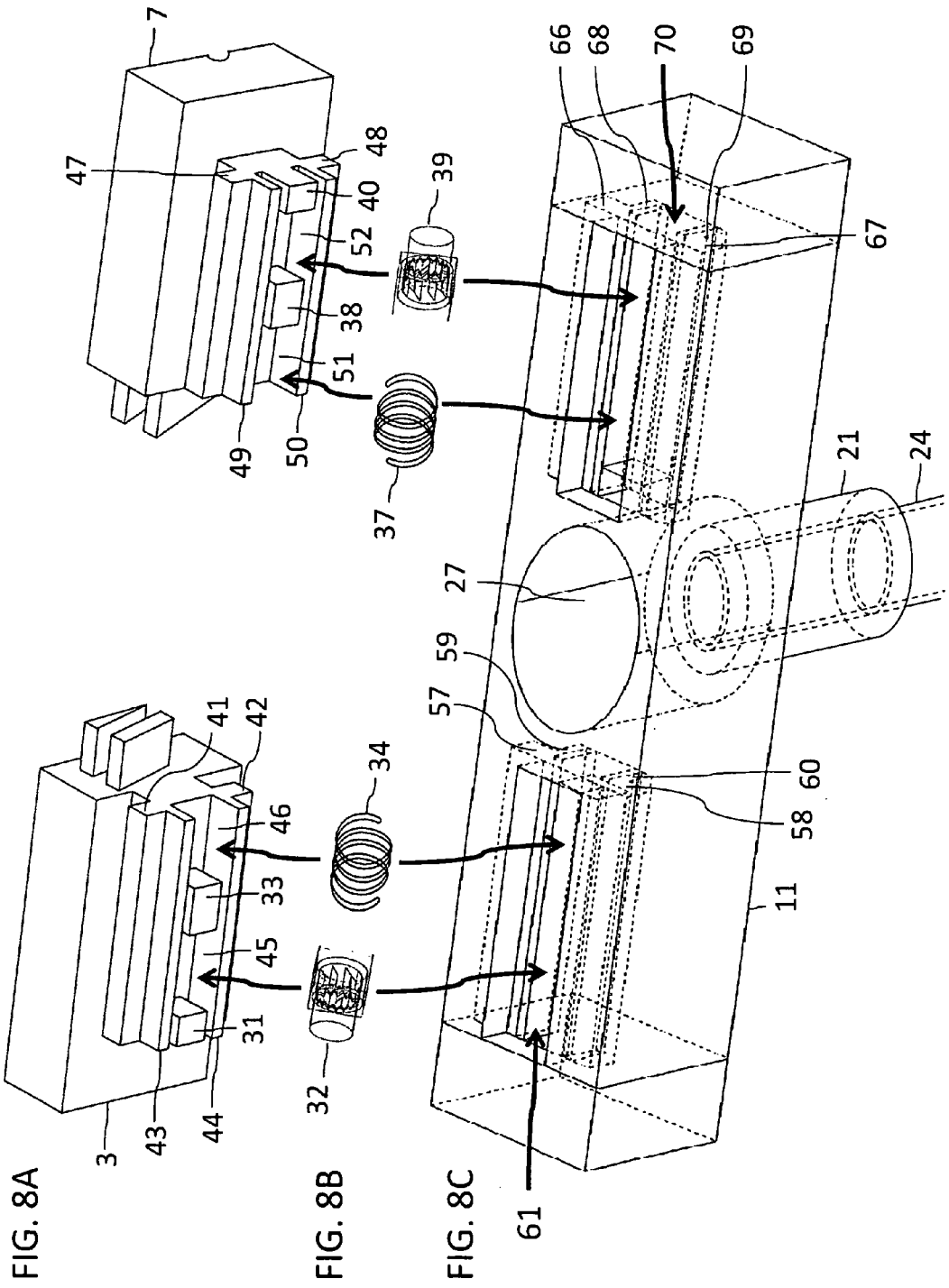

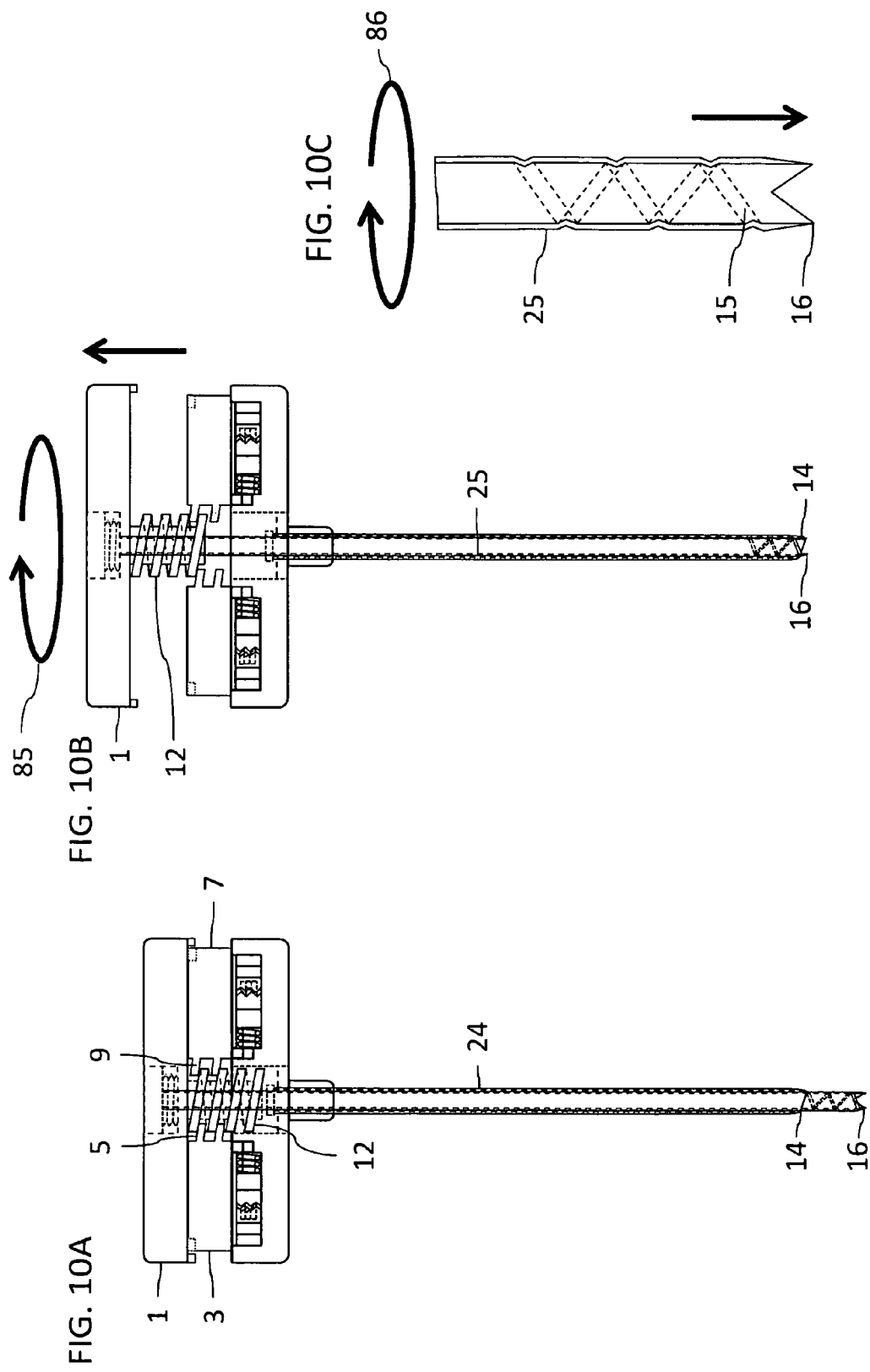

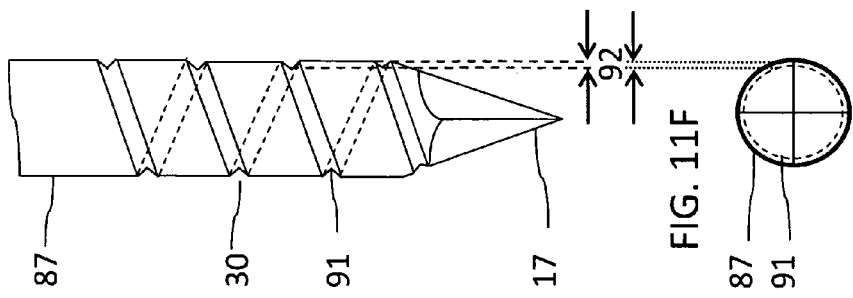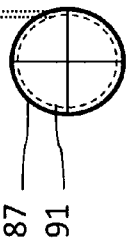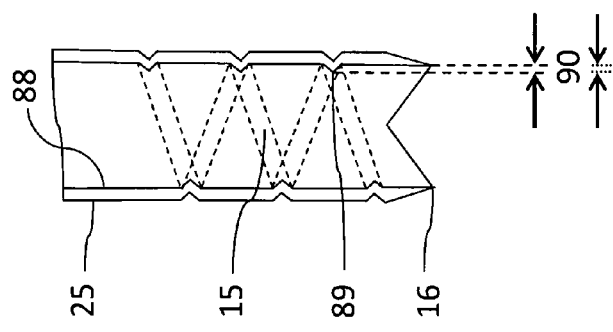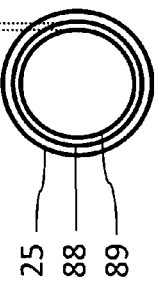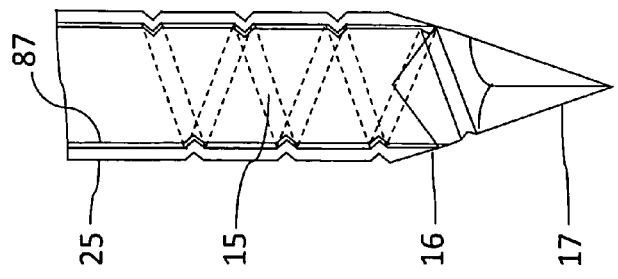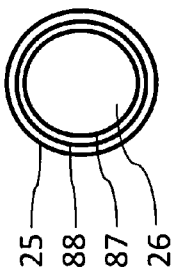

TISSUE SAMPLING APPARATUS

TECHNICAL FIELD

The present invention relates generally to the field of obtaining bone marrow samples. More specifically, the present invention provides an apparatus and methods to reliably obtain both solid and liquid marrow samples in sequence upon a single entry into a target tissue.

BACKGROUND OF THE INVENTION

Obtaining bone marrow samples for diagnostic purpose in medicine requires insertion of an instrument into a marrow space following penetration into a hard cortical bone that surrounds the marrow space. Traditionally it is done by pushing in a hollow needle that has a cutting edge or a cutting tip at its distal end. Usually two specimens, i.e., solid piece of marrow and liquid aspirate, are required for accurate assessment of potential disorders in the bone marrow. The majority of biopsies of bone marrow require at least two separate insertions of the needle, with each for a solid and a liquid sample, respectively. Acquisition of a solid piece of marrow requires threading a small linear fragment of marrow into a hollow tubular space of a needle whereas liquid marrow requires negative suctioning of the marrow into the tubular space of the needle for sampling.

Although it sounds simple and has been done in such a way for almost every patient, the requirement of a minimum of two separate insertions into hard bones has resulted in doubling of discomfort and pain on the part of patients and operator fatigue on the part of medical personnel. Consequently some physicians favor an increase in local anesthetics and sometimes heavy sedation of patients to alleviate their discomfort. Furthermore, some patients who would have a low platelet count are exposed to an increase in a risk of bleeding from the biopsy sites, and some with a low white blood cell count may have an increase in a risk of infection, when theoretically compared to a single insertion acquisition of marrow samples.

Another drawback of acquisition of solid marrow samples comes from frequent loss of the threaded sample in the hollow tubular shaft of a needle, which is yet adhered to a main body of the marrow at the distal tip of the hollow tubular shaft of a biopsy needle. Since the tubular shaft of the needle is straight and hollow, threaded-in samples are routinely lost in whole or in part when the needle is withdrawn unless the threaded-in sample is broken off at an angle from the main body of the marrow, held tight inside the hollow tube of the needle or captured inside the hollow tube. Furthermore, some diseases of the marrow such as leukemia tend to have a fragile marrow sample that gets fragmented easily. The loss of solid marrow samples necessitates repeating insertion of the needle until an adequate amount of sample is obtained, which obviously exacerbates the aforementioned problems. Wide circumferential and whirling rotation of the biopsy needle along the longitudinal axis to break off the sample has been universally accepted as one technique of biopsy yet it causes additional discomfort to patients.

Several patents have disclosed methods and devices to capture samples that are threaded in the hollow tube of the biopsy needle. Some devices utilize insertable or indented internal threads located on an inner wall of biopsy needle close to a cutting tip and some other devices have one or a plurality of capturing devices installed inside a tubular space of the needle. These devices have improved efficiency of procurement of samples but oftentimes suffer from a lack of consistency in mechanical performance. Biopsy needles with internal threads tend to have broken fragments of samples especially when the needle has not penetrated a marrow space long enough or when a cortical bone is very hard. Helical internal threads require uni-directional circumferential rotation all the way through from a beginning of insertion of the needle into a bone to a retrieval of the needle. Incidental rotations of the needle to an opposite direction may loose a sample back to a main body of the marrow. Consequently, it is not uncommon that well-trained physicians resort back to the old yet venerable Jamshidi biopsy device for consistency of mechanical performance over a wide range of patients.

The current invention aims at solving these two technical challenges, one to reduce discomfort and pain of patients and the other to dependably secure samples, by sequential acquisition of solid marrow sample followed by liquid marrow sample upon a single entry into target bone marrow and by fail-safe directional grip on solid marrow samples.

SUMMARY OF THE INVENTION

To accomplish the goals of a single entry for sequentially acquiring multiple samples of solid and liquid marrow and of securely retrieving solid marrow samples in a fail-safe mode, the current apparatus combines a rotatable handle assembly with a cutting assembly and comprises an inner cutting tube slidably placed in an outer cannula and a trocar slidably placed in the inner cutting tube.

In one embodiment, the outer cannula houses and releasably secures the inner cutting tube and serves as a conduit to aspirate liquid marrow. A distal end of the outer cannula is beveled at an angle to maximize area for aspiration of the liquid marrow. It is tapered at the distal end toward a tip to maintain tight seal around a distal end of the inner cutting tube and sharpened for entry into bone. A proximal end of the outer cannula is attached to a handle assembly of the apparatus and its attachment is strengthened by a flange encircling a proximal part of the outer cannula at a junction with the handle assembly. There is provided a hub at the proximal end of the outer cannula inside a cylindrical space located in the middle of the handle assembly, which provides attachment to syringes and connecting tubes for suctioning off the liquid marrow. Both the distal and proximal ends of the outer cannula are connected to an outer cannula shaft that is configured as cylindrically tubular.

In one embodiment, the inner cutting tube comprises a distal end that has cutting teeth at its tip, a proximal end that is connected to a part of the handle assembly and a tubular shaft connecting both ends. The distal end has helical threads located on an inner wall of said end for a length. The internal helical threads are to help forwardly advance the inner cutting tube and to secure the solid marrow sample. In another embodiment, the proximal end has a worm fixedly encircling a proximal part of an outer wall of the tubular shaft. The worm is a part of a worm drive assembly, which comprises the worm and a worm shaft of the inner cutting tube and a plurality of worm gears of the handle assembly. The worm is to help slide out the inner cutting tube longitudinally from the outer cannula by axial rotation of said worm in the worm drive assembly.

In one embodiment, both the worm and the internal helical threads of the inner cutting tube are oppositely handed to each other on axial rotation. Rotations of the worm of the inner cutting tube to pull out said tube from the outer cannula produce rotations of the internal helical threads of said tube in a distally advancing direction that securely holds the solid marrow sample inside the distal end of said tube during retrieval of said tube. Maintaining a distally advancing rotational direction of the distal end on a secured solid marrow sample while retrieving proximally the inner cutting tube helps evenly distribute a contact between said internal helical threads and said solid marrow sample over an entire length of said internal helical threads. Following retrieval of the inner cutting tube that holds the solid marrow sample, a liquid marrow sample is aspirated from the proximal end of the outer cannula.

In one embodiment, a helix angle of the internal helical threads of the inner cutting tube is more obtuse than that of the worm of said tube, along with a wider pitch of said threads than that of said worm. Both major and minor diameters of the internal threads are smaller than those of the worm. These differences result in a higher torque of the worm per rotation than a torque generated by similar rotation of the internal helical threads.

In another embodiment, an outer wall of a distal part of the tubular shaft of the inner cutting tube is helically along the longitudinal axis and inwardly pressed by a roller to produce helical grooves on said outer wall, which in turn become the internal helical threads on an inner wall of said distal part. The roller is configured as rollable round circle and helically angled to its longitudinal axis to produce continuous helical grooves on the outer wall of the tubular shaft. An outer rim of the roller is configured to produce one or a plurality of triangular shapes of the grooves on cross section. A triangular base of the helical grooves on the outer wall matches a crest of the internal threads on the inner wall of the tubular shaft. The rolling press is done before heat treatment of the metallic tubular shaft for hardening.

In one embodiment, a worm assembly of the inner cutting tube comprises a worm shaft immovably encircling the proximal part of the tubular shaft and a worm helically projecting from said shaft. Both the worm and worm shaft are connected proximally to a part of an upper handle of the handle assembly and may be molded as a single piece with said part of the handle. The worm is longitudinally located in the middle of a cylindrical space of the handle assembly and is reversibly engageable with a plurality of worm gears medially projecting from the handle assembly. Axial rotation of the worm is configured to move the tubular shaft of the inner cutting tube longitudinally along the axis of said tube.

In one embodiment, the trocar comprises a distal end that has a tissue-penetrating tip and helical grooves on an outer surface of said trocar for a length, a proximal end that has external helical threads to securely be fastened to the handle assembly and a trocar shaft that connects both ends. The external helical grooves of the distal end of the trocar are matched with the internal helical threads of the inner cutting tube in a way that when assembled together the trocar shaft provides the inner cutting tube with structural support for the part of said tube. The tip of the trocar is configured as pointed-cone-shaped with a plurality of sharpened planar facets on its outer surface and is paired with the cutting teeth of the inner cutting tube to form a single end for tissue penetration and cutting.

The handle assembly comprises an upper handle and a lower handle. In one embodiment, the upper handle may have a plurality of configurations, including a rectangular-bar shape with rounded top edges where the upper handle is gripped by an operator's hand. A top part of the upper handle has a cylindrical space in the center for a depth into said handle and a bottom part of said handle at a center is immovably connected to the proximal end of the inner cutting tube. The proximal end of the tubular shaft of the inner cutting tube penetrates the central bottom part of the upper handle and opens up to the central cylindrical space. There is provided internal helical grooves on an inner wall of the cylindrical space, which engage the external helical threads of the trocar for fastening of said trocar.

In another embodiment, a bottom of the upper handle has a pair of handle coupling mechanisms located on both lateral ends, which releasably couple the upper handle with the lower handle. The handle coupling mechanism may have one or a plurality of configurations, including a snap configuration. The upper handle is rotatable around the longitudinal axis of the inner cutting tube once the upper handle is uncoupled from the lower handle.

In one embodiment, the lower handle may have a plurality of configurations, including a rectangular-bar shape with rounded bottom edges where the lower handle is gripped by an operator's hand. The lower handle comprises a handle base and a pair of slidable members of the lower handle, which insertably are assembled with the handle base on a top part of said handle base. Both the slidable members are identical in a mirror image and may have a plurality of configurations, including a rectangular-bar shape. Both the slidable members are assembled symmetrically on each side of the lower handle base across a center of the lower handle base. There is provided a central space in between of the pair of slidable members, where both the worm and worm shaft of the inner cutting tube insertably are placed in.

In one embodiment, the slidable member has a slide-lock assembly protruding from a bottom of a main rectangular body of the slidable member. The slide-lock assembly of the slidable member may have a plurality of mechanical configurations, including slide rails and a retractable lock mechanism. The slide-lock assembly may have a plurality of linear rails along the longitudinal axis, which slide in a plurality of linear slots located inside the lower handle base. In between of the linear rails, there is provided a space along the longitudinal axis, where the retractable lock mechanism is housed. The retractable lock mechanism may have a plurality of configurations, including a mechanism used successfully for a ballpoint pen (U.S. Pat. No. 3,288,115). The retractable lock mechanism may have one or a plurality of operating components, including a compression spring, a spring butt, a modular retractable lock and a lock butt, arranged in tandem. Both the spring butt and lock butt are extended parts of the main body of the slidable member and are molded as a single piece with the main body. The modular retractable lock located in between of the lock butt and the spring butt is fixedly attached to a bottom wall of a slot of the lower handle base, which houses the slide-lock assembly. An inwardly linear push on the slidable member longitudinally toward the center of the lower handle pushes both the lock butt and spring butt to make fast the modular retractable lock and to compress the spring, respectively. A second and further push on said slidable member in a locked position unlocks the modular retractable lock and said lock moves back to its original position by re-extension of the compressed spring.

In one embodiment, the slidable member of the lower handle is configured to have a plurality of worm gear teeth projecting at a helical angle from a medial surface of the slidable member toward the worm of the inner cutting tube longitudinally inserted in the central space in between of the pair of the slidable members. Each set of the worm gear teeth on each slidable member in a neutral position is not engaged with the worm and is releasably engageable with the worm upon the inwardly linear push on each said member toward the center of the lower handle. A linear displacement from a tip of unengaged worm gear teeth to that of engaged teeth with the worm measures the same as a linear displacement from a unlocked position to a locked position of the modular retractable lock of the slide-lock assembly. The worm gear teeth remains engaged as long as the modular retractable lock is pushed and locked. Once engaged the worm, the worm gear teeth of the slidable member function as worm gear and transfer axially rotational movement of the worm to linear movement of the inner cutting tube along the longitudinal axis of said tube.

In one embodiment, a bottom of the lower handle base is fixedly connected at a center to the proximal end of the outer cannula. A tubular shaft of the outer cannula opens to a central cylindrical space of the lower handle base and is attached to a connecting hub. The central cylindrical space is configured to accommodate a plurality of types of syringe for connecting with the hub for aspirating liquid marrow.

In one embodiment, a patient is placed in a position suitable for bone marrow biopsy. Following sterilization of skin, adequate local anesthesia and a nick made in the skin by a piercing scalpel, an assembled apparatus of the present invention is introduced to a cortical bone through the nick. Upon contact with the cortical bone, the apparatus is rotated uni-directionally and forwardly pushed until said apparatus has penetrated through the cortical bone and has come into contact with a marrow space. A trocar of the apparatus is rotationally removed and said apparatus continues to be rotated uni-directionally and forwardly pushed to an optimal depth. A pair of slidable members of a lower handle are horizontally pushed in toward a center of the apparatus and locked by each modular retractable lock of a slide-lock assembly, thereby uncoupling an upper handle from the lower handle and making a plurality of worm gear teeth located on each medial surface of the slidable member engage a worm of an inner cutting tube. While the lower handle is fixed in position by one hand of an operator, the upper handle then is rotated by another hand of said operator in the same direction as said apparatus was introduced. The rotation of the upper handle in the same direction pulls out the inner cutting tube that securely contains a solid marrow sample. Following acquisition of the solid marrow sample, the slidable members are released back to their original position. A syringe matched with a hub of the lower handle base is connected to said hub and a negative suctioning is applied by pulling a plunger out inside a syringe cylinder to obtain an aliquot of liquid marrow sample. Once the liquid marrow sample is obtained, an outer cannula of said apparatus is removed. The procured solid marrow sample is pushed out by a straight stylet in a direction from a distal cutting tip to a proximal end of the inner cutting tube.

BRIEF DESCRIPTION OF THE DRAWINGS

FIG. 1 shows a schematic two-dimensional presentation of the apparatus of the present invention.

FIG. 2 shows a schematic example of an enlarged view of itemized devices of the apparatus.

FIG. 3 shows a schematic profile view of three separate assemblies of the apparatus: FIG. 3A represents an outer cannula assembly; FIG. 3B shows an inner cutting tube assembly; FIG. 3C shows a trocar assembly.

FIG. 4 shows a schematic example of slidable members of a lower handle: Shaded areas of FIG. 4A represent a profile view of a pair of the slidable members; A shaded area of FIG. 4B shows a cross-sectional lateral view of a slidable member; FIG. 4C shows a three-dimensional view of the pair of the slidable members.

FIG. 5 shows a schematic example of a lower handle base; A shaded area of FIG. 5A represents a cross-sectional lateral view; FIG. 5B shows a three-dimensional view.

FIG. 6 shows a schematic example of a retractable lock mechanism.

FIG. 7 shows a profile view of a schematic example of a slide-lock mechanism of a slidable member of a lower handle: FIG. 7A shows a slidable member in a neutral and unengaged position, assembled with the lower handle base; FIG. 7B shows the slidable member pushed in a direction of an arrow and locked by a retractable lock.

FIG. 8 shows a schematic three-dimensional illustration of individual components of a lower handle: FIG. 8A depicts a pair of slidable members showing slide rails and compartments for retractable locks and springs; FIG. 8B shows a pair of retractable locks and of springs; FIG. 8C shows a lower handle base, a flange and a proximal end of an outer cannula.

FIG. 10 shows a schematic example of a method of withdrawal of an inner cutting tube assembly from an outer cannula assembly and of securing solid marrow sample in the inner cutting tube assembly: FIG. 10A shows a pair of slidable members of a lower handle pushed in and locked, thereby uncoupling an upper handle and engaging a worm; FIG. 10B depicts a linear withdrawal of the upper handle by clockwise rotation of said upper handle; FIG. 10C shows a linear forward movement of a distal end of the inner cutting tube by the same clockwise rotation.

FIG. 11 shows a schematic example of a cutting end assembly: FIG. 11A represents a profile view of a distal part of an inner cutting tube assembled with a distal part of a trocar; FIG. 11B shows a profile view of the distal part of the inner cutting tube; FIG. 11C shows a profile view of the distal part of the trocar; FIGS. 11D through 11F show cross-sectional views of the cutting end assembly.

FIG. 12 illustrates a schematic example of a mechanism of coupling and uncoupling of a handle assembly.

FIG. 13 shows schematic examples of connection of a hub of an outer cannula assembly with different types of syringe and with an extension tube.

DETAILED DESCRIPTION OF THE DRAWINGS

Figure 2B:
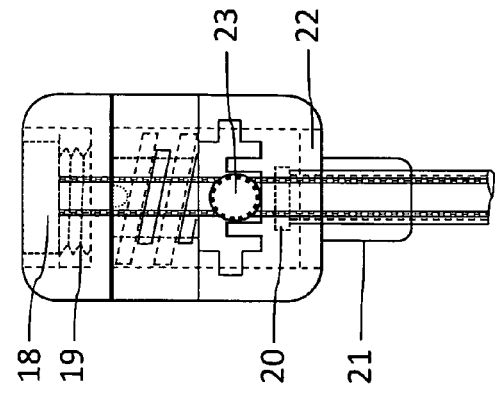
FIGS. 2A and 2B represent a profile and lateral view of a handle assembly, respectively.

As described below, the present invention provides a bone marrow tissue sampling apparatus and methods of use. It is to be understood that the descriptions are solely for the purposes of illustrating the present invention, and should not be understood in any way as restrictive or limited. Embodiments of the present invention are preferably depicted with reference to FIGS. 1 to 13, however, such reference is not intended to limit the present invention in any manner. The drawings do not represent actual dimension of devices, but illustrate the principles of the present invention.

FIG. 1 shows a schematic illustration of an example of the apparatus comprising a handle assembly A, a cutting end assembly C and a shaft assembly B that connects both the handle assembly and cutting end assembly. The handle assembly A is provided as a plurality of operating devices having one or a plurality of mechanical configurations, which houses a proximal part of the shaft assembly B in a center of said handle assembly and functions to advance or retrieve the apparatus in whole or in part and to obtain samples. The cutting assembly C is provided as a plurality of operating devices having one or a plurality of mechanical configurations, which is connected to the shaft assembly B and functions to penetrate into a target tissue and to procure samples. The shaft assembly B is provided as a plurality of operating devices having one or a plurality of mechanical configurations, which functions as a rigid hollow tubular structure to enter a target tissue and to support the cutting end assembly C.

FIG. 2 shows an enlarged view of a schematic example of individual devices of the apparatus. FIG. 2A shows a profile view of the handle assembly and FIG. 2B shows a cross-sectional lateral view of said assembly. FIG. 2C shows a schematic profile view of the cutting end assembly and FIG. 2D shows a cross-sectional view of the shaft assembly. An upper handle 1 is releasably coupled at handle coupling mechanisms 6 and 10 with both slidable members 3 and 7 of a lower handle. In a center of the upper handle 1, there is provided a central cylindrical space 2 of a certain depth to accommodate a proximal end 18 of a trocar. Referring to FIG. 2B, the proximal end 18 of the trocar is rotatably fastened by trocar fastening threads 19. The slidable members of the lower handle 3 and 7 have a plurality of worm gear teeth 5 and 9, respectively, projecting at a helical angle from a medial surface of each 3 and 7 toward a worm 12 attached to a bottom of the upper handle 1. In a neutral and unengaged position, both the worm gear teeth 5 and 9 are not engaged with the worm 12. The slidable member 3 and 7 have slide-lock assemblies 4 and 8, respectively, protruded from a bottom of said members, which irreversibly are inserted into a pair of slots of a lower handle base 11. A center of a bottom of the lower handle base 11 is penetrated by and fixedly connected to a proximal part 13 of the shaft assembly. FIG. 2B shows a lateral view of the proximal end 18 of the trocar and the trocar fastening threads 19 insertably placed in the central cylindrical space 2 of the upper handle 1. A cross sectional view of the lower handle base shows a connecting hub 20 to an outer cannula, an outer cannula flange 21, a bottom layer 22 of the lower handle base and a part of a retractable lock assembly 23 located in the middle of the slide-lock assembly.

Figure 2D:
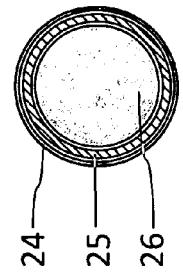
FIG. 2D shows a cross-sectional view of a shaft assembly.
Figure 2A:
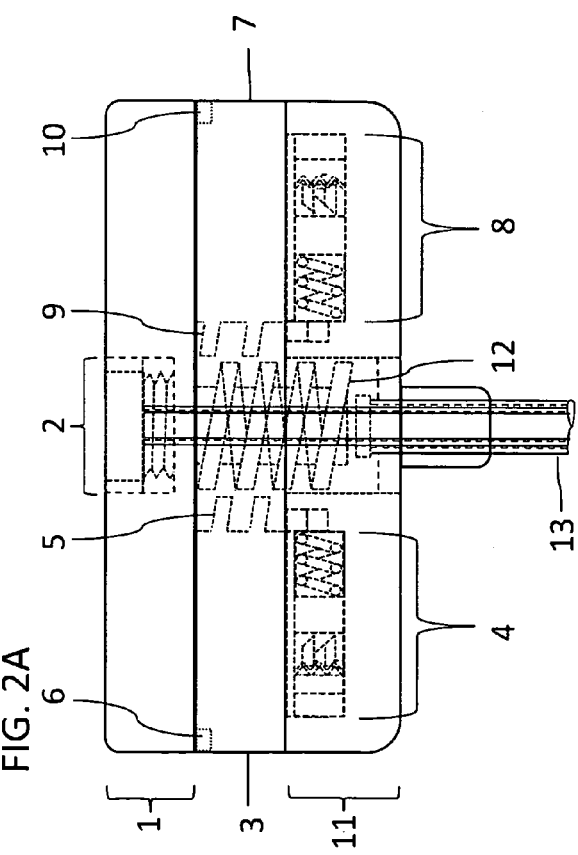
Figure 2C:
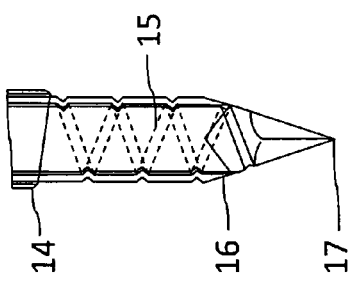
FIG. 2C shows a profile view of a cutting end assembly.

FIG. 2C shows an outer cannula tip 14, internal helical threads 15 of an inner cutting tube, a plurality of cutting teeth 16 of the inner cutting tube and a trocar tip 17. The outer cannula tip 14 is configured to increase a cross-sectional area for aspiration of liquid marrow, to maintain tight seal around a distal end of the inner cutting tube and to enter a target tissue with ease. The internal helical threads 15 of the inner cutting tube is configured to help forwardly advance the inner cutting tube and to secure solid marrow sample. FIG. 2D shows a cross-sectional view of an outer cannula 24 encircling an inner cutting tube shaft 25. A trocar shaft 26 is insertably placed inside the inner cutting tube shaft 25. Both the inner cutting tube shaft 25 and trocar shaft 26 are configured to maintain structural strength and rigidity of the shaft assembly.

FIG. 3 shows a profile view of a schematic example of three separate assemblies of the apparatus. FIG. 3A represents an outer cannula assembly that comprises the slidable members 3 and 7 of the lower handle, the lower handle base 11 and the outer cannula 24 and tip 14. A medial side of both slidable members 3 and 7 faces each opposite side in a distance to form a central space that accommodates the worm 12 and the worm shaft 29 of the inner cutting tube assembly of FIG. 3B. The bottom layer 22 at the center of the lower handle base 11 is fixedly connected to a proximal end of the outer cannula 24 and the connection joint is strengthened by the flange 21. The outer cannula 24 opens up to the central cylindrical space 27 and is connected to the connecting hub 20.

FIG. 3B shows an inner cutting tube assembly that comprises the upper handle 1, the worm 12, a worm shaft 29, the inner cutting tube shaft 25 and the cutting teeth 16. In the center of the upper handle 1, there is provided the central cylindrical space 2 and internal helical grooves 28 located on an inner wall of said central cylindrical space 2 for the proximal end 18 of the trocar and the trocar fastening threads 19. The trocar fastening threads 19 are releasably and rotatably fastened to said internal helical threads 28 when assembled. The worm shaft 29 supports the worm 12 and is fixedly encircling a proximal part of the inner cutting tube shaft 25. The upper handle 1, the worm 12 and the worm shaft 29 may be molded together as a single piece. The inner cutting tube shaft 25 is configured as cylindrically tubular, which runs longitudinally from a proximal end bordered by the internal helical grooves 28 to the cutting teeth 16. In a distal part of the inner cutting tube shaft 25, there is provided the internal helical threads 15, for a certain length to the cutting teeth 16, made by roller-pressed external helical grooves on an outer wall of the inner cutting tube shaft 25. Both the worm 12 and the internal helical threads 15 are oppositely handed to each other on axial rotation. For an example, the worm 12 is left handed and the internal helical threads 15 is right handed. For another example, the worm 12 is right handed and the internal helical threads 15 left handed. Rotation of the inner cutting tube assembly in a direction of the worm 12 to pull out the inner cutting tube assembly from the outer cannula assembly produces rotation of the internal helical threads 15 in a forward advancing direction that continues to hold a solid marrow sample without potential chances of loss of the procured sample.

FIG. 3C shows a trocar assembly that comprises the proximal end 18 of the trocar, the trocar fastening threads 19, the trocar shaft 26 and the tissue penetrating tip 17. In a distal part of the trocar shaft 26, there is provided external helical grooves 30 for a certain length to the tip 17, which rotatably slide in the inner cutting tube and are matched with the internal helical threads 15 of the inner cutting tube. The grooved part of the trocar shaft 26, when assembled with the inner cutting tube, is configured to provide the part of the inner cutting tube having the internal helical threads 15 with enough structural strength to pierce through hard cortical bones without material failure such as buckling. Once a softer marrow is reached, the trocar is removed and the inner cutting tube is rotatably advanced with less resistance. The trocar tip 17 is configured as pointed-cone-shaped with a plurality of sharpened planar facets on an external surface of said tip and is paired with the cutting teeth 16 of the inner cutting tube.

The present apparatus is assembled in a way the trocar tip 17 and the trocar shaft 26 are inserted into the inner cutting tube shaft 25 through the central cylindrical space 2, and the inner cutting tube teeth 16 and the tube shaft 25 are inserted into the outer cannula 24 through the connecting hub 20. The proximal end of the trocar 18 is secured by the trocar fastening threads 19 rotatably fastened to the internal helical grooves 28 of the inner cutting tube assembly. The inner cutting tube assembly is secured to the outer cannula assembly by the handle coupling mechanisms 6 and 9.

FIG. 4 shows a schematic example of slidable members of a lower handle. Shaded areas of FIG. 4A represent a profile view of a pair of the slidable members 3 and 7. A shaded area of FIG. 4B shows a cross-sectional lateral view of the slidable member 3. FIG. 4C shows a three-dimensional view of a pair of the slidable members 3 and 7. FIGS. 4A and 4B show bottom parts of the slidable members 3 and 7 insertably assembled with of the lower handle base 11. Referring to FIG. 2A, both the bottom parts of the slidable members are configured to have the slide-lock assembly 4 and 8 on each member, respectively, which is housed in a pair of longitudinal slots of the lower handle base 11. The slide lock assembly may have a plurality of configurations, including a set of slide rails and a retractable lock mechanism. FIG. 4A shows a profile view of the retractable lock mechanism 31 through 34 for the slidable member 3 and the other lock mechanism 37 through 40 for the slidable member 7. The retractable lock mechanism has a lock butt 31 and 40, a modular retractable lock 32 and 39, a spring butt 33 and 38 and a compression spring 34 and 37, respectively for each slidable member. Both the lock butt 31 and 40 and the spring butt 33 and 38 are extension of a main body of each slidable member, respectively, and are molded as a single piece with the main body of said member. A recess 35 is a space that accommodates linear movement of slide rails of the slidable member 3. A recess 36 accommodates similar movement of slide rails of the slidable member 7.

FIG. 4B shows a cross-sectional lateral view of the slide rails of the slidable member 3. The slide rails may have a plurality of configurations, including a pair of linearly rectangular-bar-shaped horizontal rails 41 and 42 and a pair of vertical rails 43 and 44, which slide in a plurality of linear slots inside the lower handle base 11. Both the horizontal rail and vertical rail join each other at a right angle along the longitudinal axis, which stabilizes the slide-lock assembly during sliding movement inside the slots of the lower handle base 11. FIG. 4C shows a three-dimensional view of the slidable members 3 and 7 exposing the slide-lock assemblies and the worm gear teeth 5 and 9. The slide-lock assembly of the slidable member 3 has a pair of the horizontal rails 41 and 42 and a pair of the vertical rails 43 and 44. In between of both the vertical rails 43 and 44, there is provided a space along the longitudinal axis of the slidable member 3, where the retractable lock mechanism is housed. The lock butt 31 is located behind the modular retractable lock 32 that is inserted in a compartment 45. The modular retractable lock 32 is fixedly attached to a bottom wall of the slot of the lower handle base 11 and is configured to be pushed longitudinally by the lock butt 31 of the slidable member. Said modular retractable lock 32 is configured to abut the spring butt 33 and to push said spring butt toward the compression spring 34 that is housed in a compartment 46. The slide-lock assembly of the slidable member 7 has a pair of the horizontal rails 47 and 48 and a pair of the vertical rails 49 and 50. The slidable member 7 has the same parts of the retractable lock mechanism in a mirror image as the slidable member 3, which comprises the lock butt 40, a compartment 52 for the modular retractable lock 39, the spring butt 38 and a compartment 51 for the compression spring 37.

FIG. 5 shows a schematic illustration of the lower handle base 11. A shaded area of FIG. 5A represents a cross-sectional lateral view and FIG. 5B shows a three-dimensional view. The lower handle base 11 may have a plurality of configurations, including a rectangular-bar shape that has a central cylindrical space 27 and a pair of longitudinally elongated slide rail assemblies symmetrically located on both sides of the central cylindrical space. The slide rail assembly is configured to house and guide the slide-lock assembly of the lower handle. A slide rail assembly comprises a pair of horizontal slide rail guides 53 and 54, a pair of vertical slide rail guides 55 and 56, a pair of horizontal slide rail slots 57 and 58, a pair of vertical slide rail slots 59 and 60 and a retractable lock assembly slot 61 located in between of said vertical slide rail guides 55 and 56. The other slide assembly has a similar configuration, which comprises horizontal slide rail guides 62 and 63, vertical slide rail guides 64 and 65, horizontal slide rail slots 66 and 67, vertical slide rail slots 68 and 69 and a retractable lock assembly slot 70 in between of said vertical slide rail guides 64 and 65.

FIG. 6 shows a schematic example of the retractable lock mechanism. FIG. 6A represents a two-dimensional profile view of individual components, comprising a push cylinder 71, an inner rotation cylinder 74, an outer rotation cylinder 77 and a cylinder housing 78. FIG. 6B shows a three-dimensional view of the components. The push cylinder 71 is configured to insertably house the inner rotation cylinder 74 that is fixedly attached to the outer rotation cylinder 77. Both the push cylinder 71 and rotation cylinders 74 and 77 reversibly slide in and out of the cylinder housing 78. The push cylinder may have a plurality of configurations, including a cylindrical tube that has a set of external isosceles-triangularly pointed protuberances 72 circumferentially disposed about said cylinder 71. A distal border 73 of the push cylinder 71 is configured as circularly arranged sawteeth with which the triangularly pointed protuberances 72 are matched on an outer wall of said cylinder 71. The rotation cylinders 74 and 77 may have a plurality of configurations, including a cylindrical tube that has a set of rotational cylinder protuberances 76 circumferentially disposed about said outer rotation cylinder 77. A proximal border 75 of the outer rotation cylinder 77 is configured as circularly arranged sawteeth that interdigitate with the sawteeth 73 of the push cylinder 71. A proximal end of the rotational cylinder protuberance 76 is right-triangularly pointed. The cylinder housing 78 is configured as solid rectangular box in which a cylindrical tube 83 is carved. On an inner wall of the cylindrical tube 83, there is provided a set of internal toothed splines 79 circularly disposed. Each internal toothed spline 79 is separated from the other 79 by a spline groove 80 and is configured as having a pair of triangular spline teeth 82 with an in-between spline recess 81 at a distal tip of said spline. Referring to FIG. 5, a bottom wall of the cylinder housing 78 is immovably attached to the wall of the retractable lock assembly slot 61 and the other cylinder housing 78 is immovably attached to the opposite retractable lock assembly slot 70.

Figure 6A:
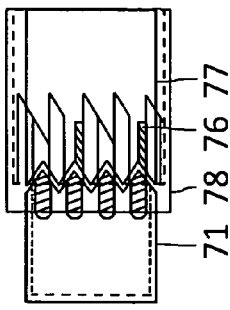
FIG. 6A represents a two-dimensional profile view of individual components.
Figure 6B:
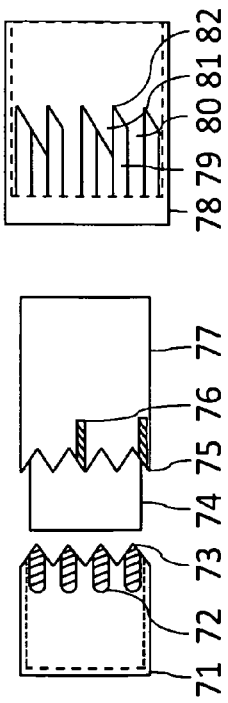
FIG. 6B shows a three-dimensional view of the components.
Figure 6C:
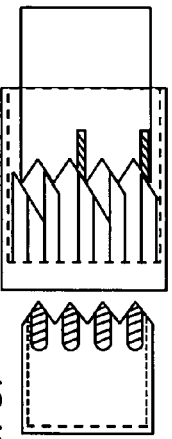
FIG. 6C shows a cross-sectional lateral view of the components.
Figure 6D:
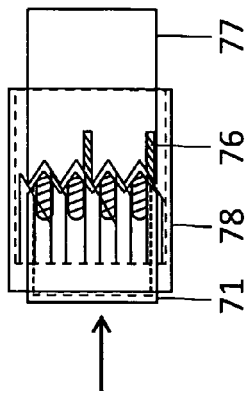
FIG. 6D shows a profile view of the components in a neutral and unengaged position.
Figure 6E:
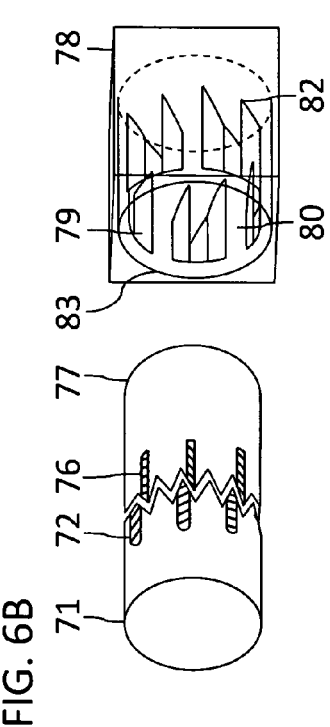
FIG. 6E shows a profile view of the components engaged and locked.
Figure 6F:
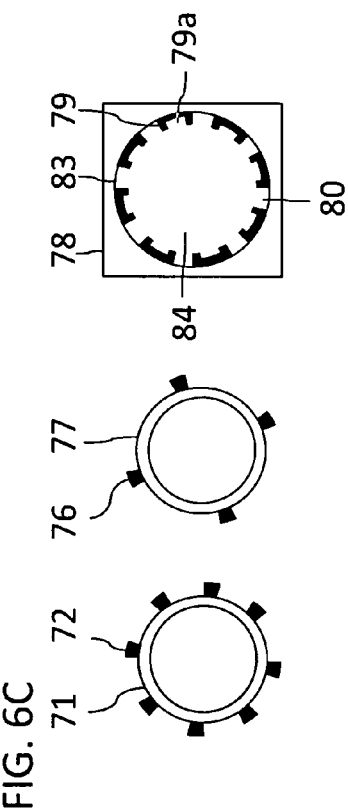
FIG. 6F shows a profile view of the locked components, with a push cylinder depicted away from the locked components for illustration.

FIG. 6C shows a cross-sectional view of the components. A cylindrical space 84 is formed by the cylindrical tube 83 inside the cylinder housing 78, in and out of which the push cylinder 71 and the rotation cylinders 74 and 77 slide. There is provided a longitudinally linear depression 79a in the middle of each internal toothed spline 79. FIG. 6D shows a profile view of the assembled components of the retractable lock assembly in a neutral and unengaged position. Once a proximal end of the push cylinder 71 is pushed distally, as shown in FIG. 6E, the outer rotation cylinder 77 is pushed distally through the cylindrical space 84 and triangular tips of the rotation cylinder protuberances 76 are rotatably held by tapered slopes of the spline teeth 82, as shown in FIG. 6F. In FIG. 6F, the push cylinder is depicted away from the cylinder housing for an illustrative purpose. A second push on the push cylinder 71 inserts the external pointed protuberances 72 of said push cylinder in the linear depressions 79a of the internal toothed splines 79 and rotatably pushes the rotation cylinder protuberances 76 distally, thereby releasing proximally back said protuberances 76 through the spline grooves 80.

FIG. 7 shows a profile view of a schematic example of a slide-lock mechanism of the slidable member 3 of the lower handle. A part of the lower handle base 11 is depicted for an illustrative purpose. FIG. 7A shows the slidable member 3 in an unengaged and neutral position, insertably assembled with the lower handle base 11. In a space provided in the lower handle base 11, the lock butt 31 abuts on the proximal end of the push cylinder 71 of the retractable lock assembly and the spring butt 33 abuts on a distal end of the outer rotation cylinder 77. The spring butt 33 is located posterior to the compression spring 34. The cylinder housing 78 is fixedly attached to the bottom wall of the slot of the lower handle base 11. As illustrated in FIG. 7B, a linear push in a direction of an arrow on the slidable member toward the center of the lower handle pushes both the lock butt 31 and spring butt 33. Referring to FIGS. 6D-6F, the outer rotation cylinder 77 is pushed inside the cylinder housing 78 by the push cylinder 71 and is reversibly anchored at the tapered slopes of the spline teeth 82. The spring butt 33 compresses the compression spring 34, thereby allowing the slidable member 3 to move toward the center of the lower handle. Once moved in, the slidable member remains in a locked position until a second and further push on said slidable member 3 toward an end of the recess 35 releases said outer rotation cylinder 77 from said cylinder housing 78. Once released from the locked position, said slidable member 3 moves back to the neutral position by re-extension of the compression spring 34.

FIG. 8 shows a schematic three-dimensional illustration of individual components of the lower handle. FIG. 8A depicts a pair of the slidable members 3 and 7 showing the slide rails 41~44 and 47~50, and the compartments 45-46 and 52-51 for the retractable locks and the springs, respectively. FIG. 8B shows a pair of the retractable locks 32 and 39, and of the springs 34 and 37. The retractable locks 32 and 39 are insertably and immovably assembled in the slide-lock assembly slots 61 and 70 of the lower handle base 11, respectively. Said immovably assembled locks 32 and 39 get into the slide lock compartments 45 and 52 of the slidable members of 3 and 7, respectively. The compression springs 34 and 37 are inserted in the spring compartments 46 and 51 of the slidable members 3 and 7, respectively. FIG. 8C shows the proximal end of the outer cannula 24 that is fixedly connected to the center of the bottom of the lower handle base 11 and opens to the central cylindrical space 27. The attachment of the proximal part of the outer cannula 24 to the bottom of the lower handle base 11 is strengthened by the flange 21 encircling said proximal part. The horizontal slide rails 42 and 41 of the slidable member 3 slide in and out of the slide rail slots 57 and 58 of the lower handle base 11, respectively, within the slide-lock assembly slot 61. The vertical slide rails 43 and 44 of the slidable member 3 slide in and out of the slide rail slots 60 and 59 of said lower handle base 11, respectively. Similarly, the horizontal slide rails 47 and 48 and the vertical slide rails 49 and 50 of the slidable member 7 slide in and out of the slide rails slots 67 and 66, and 69 and 68 within the slide-lock assembly slot 70 of the lower handle base 11.

Figure 9A:
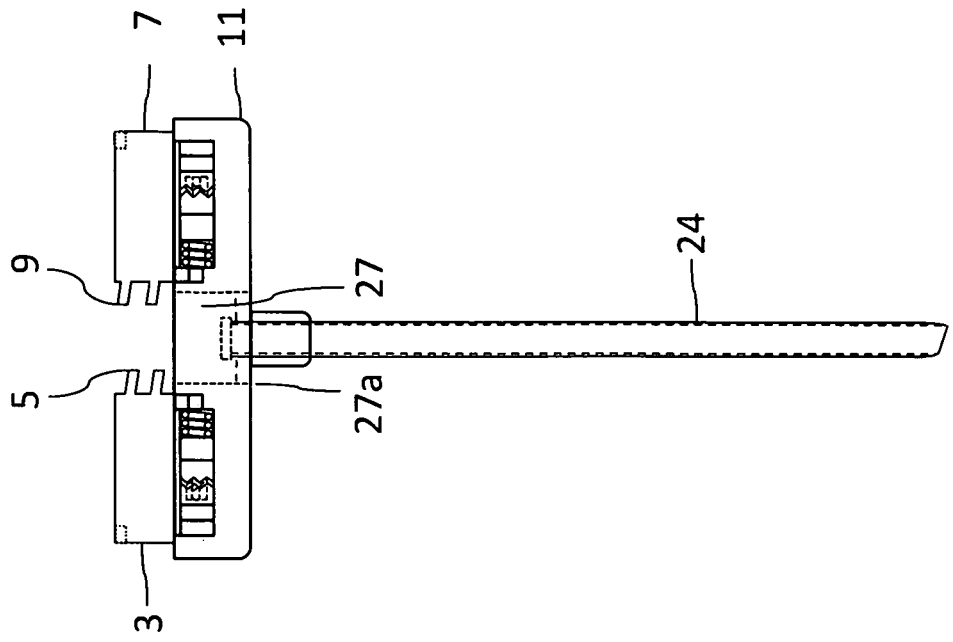
FIGS. 9A and 9B show a schematic illustration of a profile view of an outer cannula assembly in a neutral position and in an engaged position, respectively.
Figure 9B:
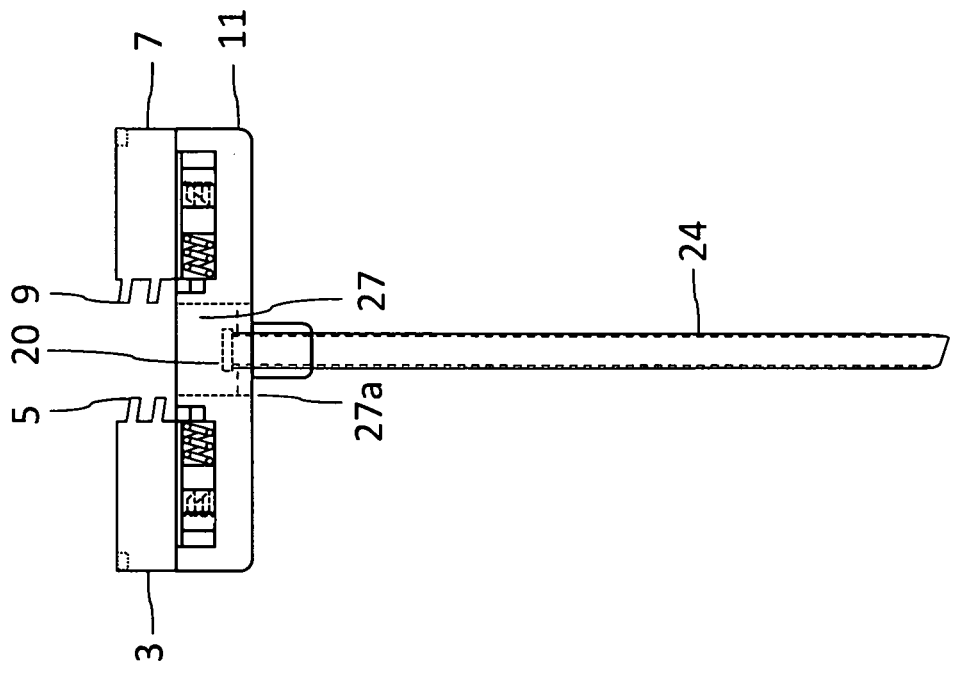

FIG. 9 shows a schematic illustration of a profile view of the outer cannula assembly with the outer cannula 24 in full assembly with the lower handle assembly of 3, 7 and 11. In a neutral and unengaged position depicted in FIG. 9A, both the slidable members 3 and 7 align with the lower handle base 11 on lateral borders of said handle base and tips of both worm gear teeth 5 and 9 align with an inner wall 27a of the central cylindrical space 27. When both the slidable members 3 and 7 are pushed toward the center of the lower handle and locked, shown in FIG. 9B, the tips of the worm gear teeth 5 and 9 cross the inner wall 27a of the central cylindrical space 27 to engage the worm 12 illustrated in FIG. 3B.

FIG. 10 shows a schematic example of a method of withdrawal of the inner cutting tube assembly from the outer cannula assembly and of securing solid marrow sample in the inner cutting tube 25. FIG. 10A shows both the slidable members 3 and 7 of the lower handle centrally pushed in and locked, thereby uncoupling the upper handle 1 and engaging the worm 12. The cutting teeth 16 of the inner cutting tube 25 is located distally to the outer cannula tip 14. In this particular example of a configuration, the worm 12 is left handed as shown in FIG. 10B and the internal helical threads 15 of the inner cutting tube 25 as shown in FIG. 10C is right handed. Clockwise rotations 85 of the upper handle 1 rotate up the worm 12 and pull off the inner cutting tube 25 from the outer cannula 24, as illustrated in FIG. 10B. As the outer cannula assembly remains unchanged for its position, a pulling-off of the inner cutting tube'25 withdraws the cutting teeth 16 of the inner cutting tube through the outer cannula tip 14. Rotations 86 of the inner cutting tube 25 in the same clockwise direction as 85 maintains a forward linear movement of the distal part of the inner cutting tube 25, which continues to make the internal helical threads 15 hold fast a procured solid marrow sample. Referring to FIG. 3, a helix angle of the internal helical threads 15 is configured as more obtuse than that of the worm 12 and a pitch of the internal helical threads 15 is wider than that of the worm 12. Both major and minor diameters of the internal helical threads 15 are configured to be smaller than those of the worm 12. Since these differences result in a higher torque of the worm 12 upon rotation than a torque generated by similar rotation of the internal helical threads 15, the clockwise rotations of the upper handle 1 pulls out the inner cutting tube 25 with said procured solid marrow sample held inside the distal part of the inner cutting tube 25.

FIG. 11 shows a schematic example of one of configurations of the cutting end assembly. FIGS. 11A and 11B represent a profile view of the distal part of the inner cutting tube 25 releasably assembled with the distal part of the trocar 26. The distal part of the inner cutting tube 25 is configured as cylindrically tubular. An outer wall of the distal part of the inner cutting tube 25 is inwardly and helically roller-pressed to produce triangularly wedge-shaped helical grooves on the outer wall, which become triangular internal helical threads 15 on the inner wall 88 toward the cutting teeth 16 of the inner cutting tube 25. An inner diameter of a crest 89 of the internal helical threads 15 is smaller than a diameter of a circumference of the inner wall 88 by twice a thread depth 90. The crest 89 spirally holds fast a solid marrow sample. FIG. 11C shows a profile view of the distal part of the trocar 26, configured as cylindrical rod with an outer wall of 87 and the trocar tip 17. The outer wall 87 is ground helically to form helical grooves 30 that are configured match the internal helical threads 15 of the inner cutting tube 25. A groove depth 92 between the outer wall 87 and a groove base 91 is configured to match the thread depth 90 of the internal helical threads 15. The tip 17 of the trocar 26 is configured as pointed-cone-shaped with a plurality of sharpened planar facets on an outer surface of said tip and is paired with the cutting teeth 16 of the inner cutting tube 25 to form a single cutting end for tissue penetration and cutting. FIGS. 11D through 11F show cross-sectional views of the cutting end assembly.

Figures 12A, 12B:
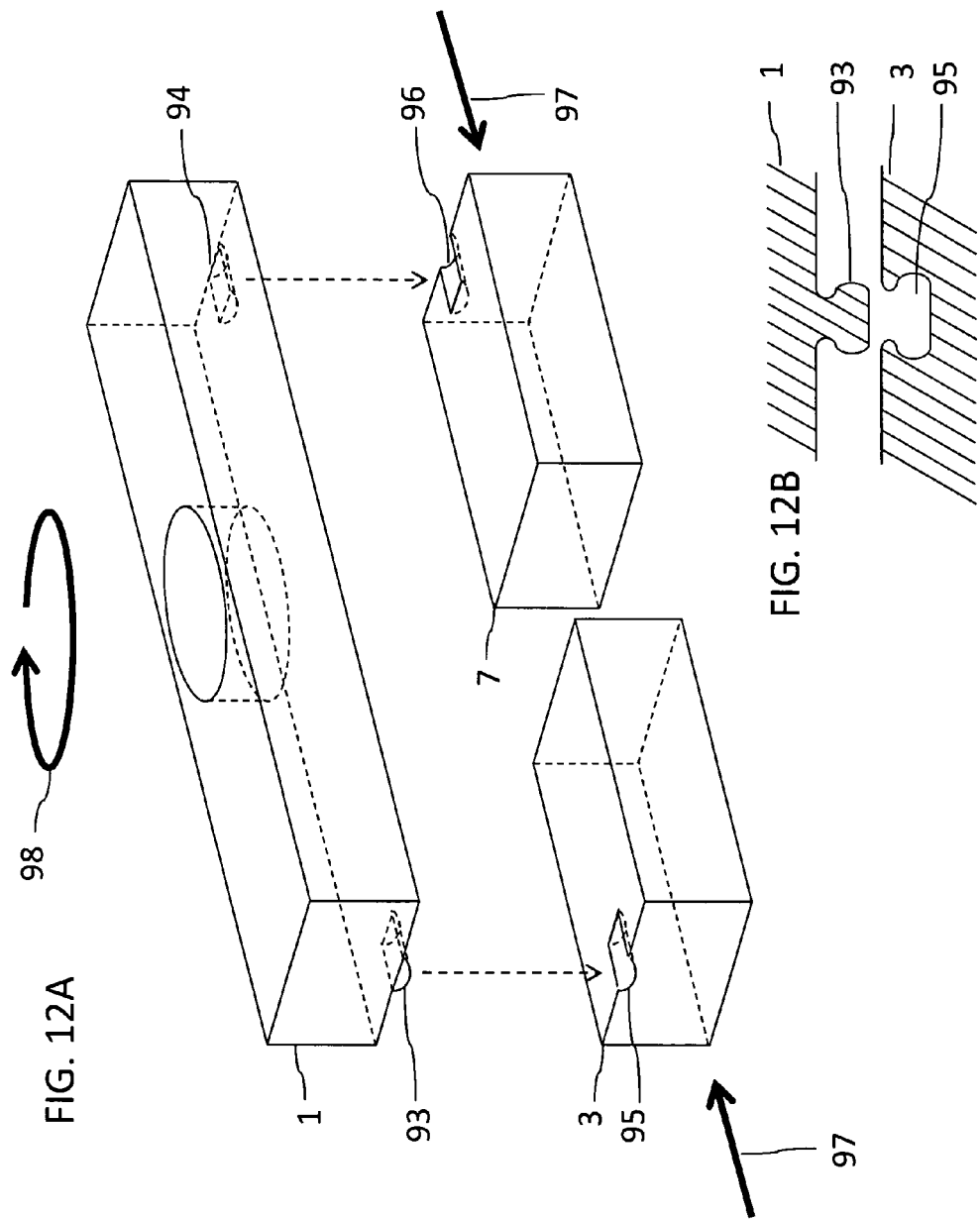
FIG. 12A depicts a sequence of a pair of slidable members pushed in toward a center of a lower handle followed by rotation of an upper handle.
FIG. 12B shows a schematic example of a cross-sectional view of a handle coupling having a snap configuration.

FIG. 12 illustrates a schematic example of a mechanism of coupling and uncoupling of the handle assembly. FIG. 12A shows a coupling of a pair of the slidable members 3 and 7 of the lower handle with the upper handle 1 through a pair of coupling projections 93 and 94 releasably inserted to a pair of coupling recesses 95 and 96, respectively, of both the slidable members 3 and 7. Uncoupling of the upper and lower handles starts with the slidable members 3 and 7 pushed to the center of the handle assembly as illustrated in 97. Both the coupling recesses 95 and 96 release the coupling projections 93 and 94 of the upper handle 1, respectively, allowing said upper handle 1 to be rotated in a direction 98. The coupling may have a plurality of configurations, including a snap configuration as cross-sectionally shown in FIG. 12B. In this snap configuration, the coupling projection 93 of the upper handle 1 is pushed to snap into the coupling recess 95 of the slidable member 3 for coupling.

Figure 13B:
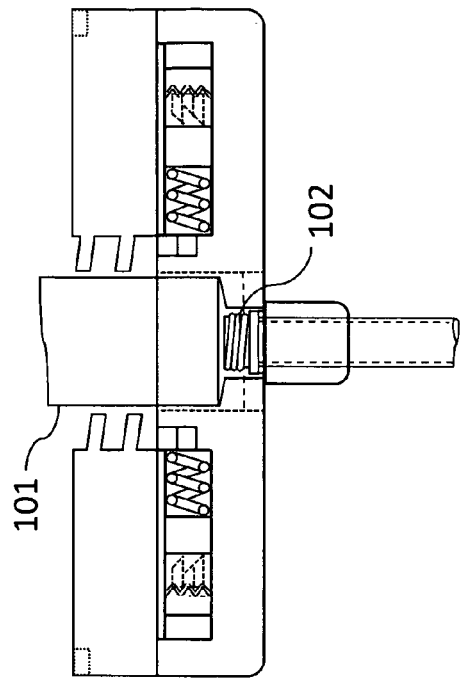
FIG. 13B shows a connection with a Luer lock syringe.
Figure 13C:
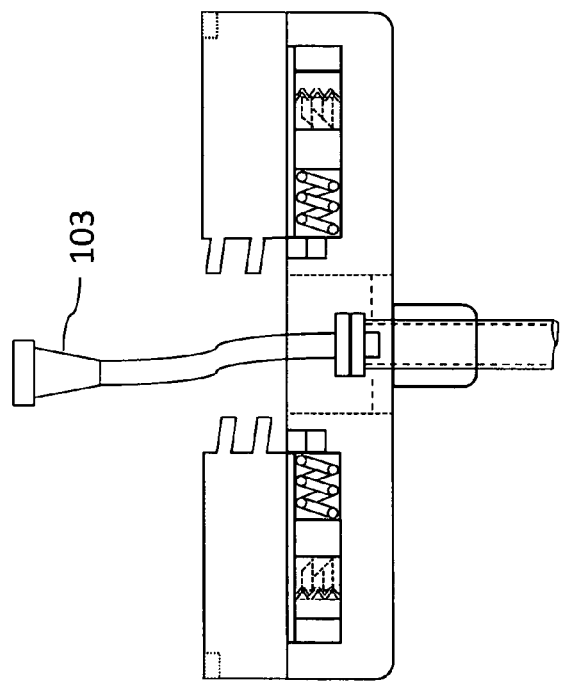
FIG. 13C shows a connection with an extension tube.
Figure 13A:
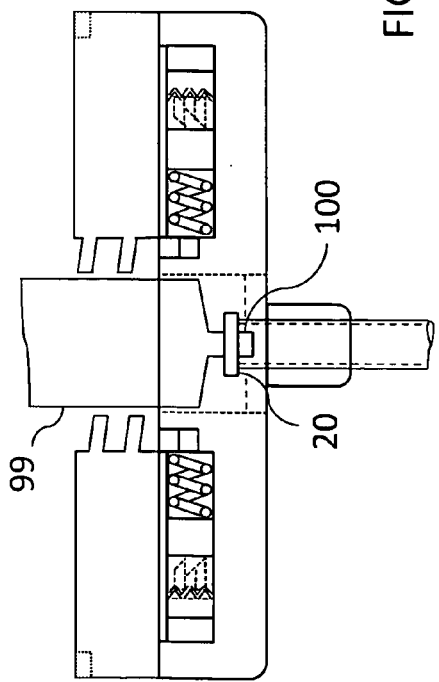
FIG. 13A shows a connection of the hub with a non-Luer lock syringe.

FIG. 13 shows profile views of schematic examples of connection of the hub 20 of the outer cannula assembly with different types of syringe and with an extension tube. FIG. 13A shows a connection of the hub 20 with a non-Luer lock syringe 99. In this example, the hub 20 has a cylindrically tubular lumen that a tubular syringe tip 100 is inserted in. FIG. 13B shows a connection with a Luer lock syringe 101. For connection with a Luer lock syringe, the hub 20 is configured with external helical threads that are releasably fastened with an internally helically grooved syringe tip 102. FIG. 13C shows a connection with an extension tube 103. The hub 20 is configured as cylindrically tubular, similar to the example in FIG. 13A.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A tissue sampling apparatus comprising an outer cannula assembly, having a proximal end, a distal end, and a cannula connecting said proximal and distal ends; an inner cutting tube assembly, having a proximal end, a distal end, and a tubular shaft connecting the proximal and distal ends of said inner cutting tube assembly, wherein the inner cutting tube assembly is coaxially insertable in the outer cannula assembly, wherein the inner cutting tube assembly is configured to penetrate tissue and secure a solid tissue sample such that the solid tissue sample is releasably and rotatably retrievable in a longitudinal manner from within the outer cannula assembly by axial rotation of said inner cutting tube assembly, wherein the inner cutting tube assembly is configured to securely contain the solid tissue sample inside said distal end of said inner cutting tube assembly;

a trocar, having a proximal end, a distal end, and a trocar shaft connecting the proximal and distal ends of said trocar, wherein the trocar is coaxially insertable in the inner cutting tube assembly, wherein the trocar is configured to penetrate into the tissue, wherein the trocar shaft is spirally grooved on an outer surface thereof at the distal end of said trocar to match spiral grooves on an inner surface of the tubular shaft of the inner cutting tube assembly so as to act as a structural support for said inner cutting tube assembly; and a handle assembly having an upper handle and a lower handle, wherein the handle is configured to provide operational control of the apparatus;

wherein the upper handle is immovably connected to the proximal end of the inner cutting tube assembly at the proximal end of the inner cutting tube assembly;

wherein the upper handle has a means disposed on a lower surface of said upper handle for reversibly anchoring an upper portion of the lower handle to the lower surface of said upper handle;

wherein the upper handle is configured to axially rotate the inner cutting tube assembly when the upper handle is released from said lower handle; and wherein the lower handle is immovably connected to the proximal end of the outer cannula assembly at the proximal end of the outer cannula assembly;

wherein the lower handle comprises a pair of slidable members configured to transmit the axial rotation of said inner cutting tube assembly to a longitudinal movement of said inner cutting tube assembly; and wherein the inner cutting tube assembly provides a space in a center of said lower handle located in between said pair of said slidable members for aspirating a liquid tissue sample.

2. The tissue sampling apparatus according to claim 1, wherein the lower handle further comprises a lower handle base, which provides the space in the center of said lower handle, wherein the inner cutting tube assembly is configured to move in and out of the space in the center of said lower handle, wherein the lower handle base is configured to accommodate an aspiration syringe in said space in the center of said lower handle;

wherein the pair of slidable members are configured to reversibly engage the inner cutting tube assembly;

wherein each of the pair of slidable members comprises a slide-lock assembly configured to reversibly lock the respective slidable member in and unlock the respective slidable member from a respective position of said lower handle base;

wherein the pair of slidable members provide said inner cutting tube assembly with a reversible worm gear arrangement to transmit the axial rotation of said inner cutting tube assembly to the longitudinal movement of said inner cutting tube assembly;

wherein each of the slide-lock assemblies is configured to reversibly slide in a corresponding structure in the lower handle base such that each of the pair of slidable members is configured to horizontally slide toward and from a center of the lower handle base, wherein each of the slide-lock assemblies is configured to slide in a first direction in the corresponding structure in the lower handle base such that a distance between the pair of slidable members shortens in length and the pair of slidable members lock in the respective position of the lower handle base and to slide in a second direction in the corresponding structure in the lower handle base such that the distance between the pair of slidable members increases in length and the pair of slidable members unlock from the respective positions of the lower handle base.

3. A method of tissue sampling, comprising:
providing the tissue sampling apparatus of claim 2; and
reversibly locking each of the pair of slidable members when the each of the pair of slidable members of said lower handle engages the inner cutting tube assembly.

4. The tissue sampling apparatus according to claim 1, wherein the inner cutting tube assembly comprises a worm helically attached to a worm shaft;

wherein the pair of slidable members and the worm form a reversible worm gear arrangement to transmit the axial rotation of said inner cutting tube assembly to the longitudinal movement of said inner cutting tube assembly;

wherein the reversible worm gear arrangement to transmit the axial rotation of the inner cutting tube assembly to the longitudinal movement of the inner cutting tube assembly comprises a plurality of worm gear teeth, which are part of the slidable members of the lower handle;

wherein the plurality of the worm teeth are configured to reversibly and rotatably engage the worm of the inner cutting tube assembly such that the plurality of worm gear teeth are configured to transmit axial rotation of said worm of said inner cutting tube assembly to the longitudinal movement of said inner cutting tube assembly;

wherein the worm gear shaft immovably encircles a part of the proximal end of the inner cutting tube assembly, wherein the worm helically projects from the worm gear shaft, and wherein the worm gear shaft provides the worm with attachment to said inner cutting tube assembly.

5. A method of tissue sampling, comprising:
providing the tissue sampling apparatus of claim 4; and,
reversibly engaging and disengaging the worm of the inner cutting tube assembly by sliding movements of the slidable members of the lower handle.

6. A method of tissue sampling, comprising:
providing the tissue sampling apparatus of claim 4; and
moving said inner cutting tube assembly longitudinally along a longitudinal axis of the inner cutting tube assembly by axially rotating the inner cutting tube assembly.

7. A method of tissue sampling, comprising:
providing a tissue sampling apparatus comprising an outer cannula assembly, an inner cutting tube assembly, and a trocar;

wherein the outer cannula assembly has a proximal end, a distal end, and a cannula connecting said proximal and distal ends;

wherein the inner cutting tube assembly has a proximal end, a distal end, and a tubular shaft connecting the proximal and distal ends of said inner cutting tube assembly, wherein the inner cutting tube assembly is insertably and coaxially placed in the outer cannula assembly, wherein the inner cutting tube assembly is configured to penetrate soft tissue and secure a solid tissue sample, wherein the inner cutting tube assembly is releasably and rotatably retrievable longitudinally from within the outer cannula assembly by axial rotation of said inner cutting tube assembly, and wherein the inner cutting tube assembly is configured to securely contain the solid tissue sample inside said distal end of said inner cutting tube assembly;

wherein the trocar has a proximal end, a distal end, and a trocar shaft connecting the proximal and distal ends of said trocar, wherein the trocar is insertably and coaxially placed in the inner cutting tube assembly, wherein the trocar is configured for penetration into the soft tissue, and wherein the trocar is spirally grooved on an outer surface thereof with external helical grooves at the distal end of said trocar so as to match internal helical threads on an inner surface of the tubular shaft of the inner cutting tube assembly at the distal end of the inner cutting tube assembly for structural support of said inner cutting tube assembly;

rotatably and forwardly pushing a proximal end of the tissue sampling apparatus to advance a distal end of the tissue sampling apparatus through the soft tissue so as to penetrate a hard tissue located underneath said soft tissue for a length;

rotating said proximal end of said tissue sampling apparatus so as to advance said distal end of said tissue sampling apparatus such that penetration of said hard tissue is made in one rotational direction;

releasing the trocar from within the inner cutting tube assembly by rotations of the proximal end of said trocar by (1) releasing the distal end of said trocar with axial rotation of the external helical grooves of said trocar over the internal helical threads of the distal end of said inner cutting tube assembly and followed by (2) longitudinal withdrawal of the trocar from within said inner cutting tube assembly in which the inner cutting tube assembly remains stationary inside the outer cannula assembly;

forwardly and rotationally advancing the outer cannula assembly and the inner cutting tube assembly in said one rotational direction inside said hard tissue for an additional length;

pushing a pair of slidable members of a lower handle of the outer cannula assembly concentrically toward an axis of said outer cannula assembly so as to uncouple an upper handle of the inner cutting tube assembly from said lower handle and to make worm gear teeth of said slidable members reversibly engage a worm disposed on a portion of an outer wall of said inner cutting tube assembly such that a reversible worm gear arrangement is formed between said worm gear teeth of said slidable members and said worm of said inner cutting tube assembly;

axially rotating the upper handle of said inner cutting tube assembly in the one rotational direction to retrieve said inner cutting tube assembly from within said outer cannula assembly;

rotatably retrieving a tissue sample of the hard tissue contained inside said distal end of said inner cutting tube assembly from within said outer cannula assembly in said one rotational direction; and wherein a hub located at a proximal end of said lower handle of said outer cannula assembly serves as a conduit for a liquid sample following the step of rotatably retrieving said tissue sample of said hard tissue and before withdrawing the tissue sampling apparatus from the soft tissue.

* * * * *